US007731308B1

(12) United States Patent
Riemer

(10) Patent No.: US 7,731,308 B1

(45) Date of Patent: Jun. 8, 2010

(54) SECURE MEDICATION CONTAINER FOR USE BY MEDICAL PERSONNEL

(76) Inventor: David Lester Riemer, 360 Buckingham Blvd., Whitewater, WI (US) 53190

( * ) Notice: Subject to any disclaimer, the term of this patent is extended or adjusted under 35 U.S.C. 154(b) by 912 days.

(21) Appl. No.: 11/328,838

(22) Filed: Jan. 10, 2006

Related U.S. Application Data

(60) Provisional application No. 60/643,740, filed on Jan. 14, 2005.

(51) Int. Cl.
*A61B 19/02* (2006.01)

(52) U.S. Cl. .................... 312/209; 312/138.1; 312/307; 312/310

(58) Field of Classification Search .............. 312/330.1, 312/304, 306, 138.1, 209, 307, 310, 204; 49/40, 41; 70/279.1, 278.1, 50; 220/377, 220/254.9, 254.1, 350, 345.4
See application file for complete search history.

(56) References Cited

U.S. PATENT DOCUMENTS 262,312 A * 8/1882 Rearden .................... 312/280
2,722,469 A * 11/1955 Kosovsky .................. 312/310
3,041,957 A 7/1962 Liptay
3,070,086 A * 12/1962 Smith et al. .................. 600/22
3,529,590 A * 9/1970 Grosholz .................... 600/22
3,915,526 A 10/1975 Weiman
4,321,913 A 3/1982 Maluta et al.
4,387,534 A * 6/1983 Lewandowski et al. ..... 312/204
4,588,237 A 5/1986 Marder
4,651,544 A * 3/1987 Hungerford ................ 70/279.1
4,794,727 A 1/1989 Smith
4,948,154 A 8/1990 Guggenheim
5,048,857 A 9/1991 Stevens
5,465,841 A 11/1995 Wilson et al.
5,524,945 A * 6/1996 Georgopoulos et al. . 292/307 A
5,826,447 A * 10/1998 Campbell .................... 70/164
5,871,243 A * 2/1999 Wenk ......................... 292/320
5,951,129 A * 9/1999 Stein ..................... 312/249.13
6,059,388 A * 5/2000 Wheatley, Jr. ............... 312/204
7,063,227 B2 * 6/2006 Looker ....................... 220/350

FOREIGN PATENT DOCUMENTS

CH 671508 * 9/1989 ................ 312/209
DE 3917875 * 6/1990

* cited by examiner

*Primary Examiner*—Hanh V Tran
(74) *Attorney, Agent, or Firm*—Craig A. Fieschko, Esq.; DeWitt Ross & Stevens S.C.

(57) ABSTRACT

A medication container is designed for secure storage of medications and other controlled substances. The container top has a sloped configuration which resists the stacking of medical files and other objects atop it (which might obscure view of the container), and it also includes a curved sliding front door allowing both a frontal and top view of medications within the container. The door is locked by use of two separate locks, one intended for a pharmacist or other medication control officer, and one by the personnel administering the medication to patients, whereby either of these parties may independently access the interior of the container. The container is also preferably designed to rapidly have a removable medication tray installed within or removed from its interior, and to rapidly be fixed to a medication cart, patient bedside table, or other structure.

19 Claims, 2 Drawing Sheets

SECURE MEDICATION CONTAINER FOR USE BY MEDICAL PERSONNEL

CROSS-REFERENCE TO RELATED APPLICATIONS

This application claims priority under 35 USC §119(e) to U.S. Provisional Patent Application 60/643,740 filed 14 Jan. 2005, the entirety of which is incorporated by reference herein.

FIELD OF THE INVENTION

This document concerns an invention relating generally to containers for securing items, and more specifically to containers for securing medications for access and dispensation by authorized personnel.

BACKGROUND OF THE INVENTION

Health care workers and facilities are often subject to stringent rules regarding medication security. Medications, particularly those that are habit-forming and/or are subject to illegal resale or other misuse, must be kept in a secure location when they are not being dispensed and/or administered. Common additional requirements are that the current locations of all medications must be tracked, their quantities must be frequently audited to guard against theft and/or loss, and the personnel having possession of the medications must be logged. Unfortunately, these requirements can be difficult to meet, particularly in large hospital and nursing home facilities. Anesthesiologists, nursing staff, and others who dispense medications must often see numerous patients during the course of a workday, and it is extremely inconvenient for them to have to repeatedly contact a medication control officer or access a secure storage area every time a controlled medication is to be administered. Thus, personnel often disregard some or all of the foregoing requirements, which can in turn lead to problems such as regulatory fines, loss and/or theft of medication, and/or administration of the wrong type or amount of medication. To illustrate, in many large hospitals and nursing facilities, nurses and other staff make their rounds by visiting many patients in succession, usually carrying the supplies for these patients on a service cart which they wheel along their routes. Staff will often stockpile the medications for the patients to be visited on some portion of their service carts, e.g., on the cart platform, which tends to make the medications easy to steal or lose. Otherwise, staff may wish to conveniently store a patient's medications in the patient's room, which can also lead to loss or theft (as well as patient self-dosing problems). It would therefore be useful if medical personnel had some means of readily securing medications on their service carts or in other selected convenient locations, such as within patients' rooms, at nurses' stations adjacent clusters of patient rooms, etc.

SUMMARY OF THE INVENTION

The invention involves a medication storage container which is intended to at least partially solve the aforementioned problems. To give the reader a basic understanding of some of the advantageous features of the invention, following is a brief summary of preferred versions of the container, with reference being made to the accompanying drawings to enhance the reader's understanding. Since this is merely a summary, it should be understood that more details regarding the preferred versions may be found in the Detailed Description set forth elsewhere in this document. The claims set forth at the end of this document then define the various versions of the invention in which exclusive rights are secured.

Referring to the drawings, FIG. 1 illustrates a preferred version of the medication storage container at the reference numeral 100, with a medication tray 102 within its container interior 104, with the container door 106 (which is at least substantially transparent) closed, and with an override key 108 inserted in a keyhole 110 to lock or unlock the container door 106. FIG. 2 then illustrates the container 100 with the container door 106 open, and with the medication tray 102 partially pulled out of the container interior 104. FIG. 3 then shows the container 100 from another vantage point with the container door 106 closed, and without the medication tray 102. The storage container 100 includes a base unit 112 which substantially surrounds the container interior 104, with the container door 106 being movably affixed to the base unit 112 to move between its open position (as in FIG. 2) and its closed position (as in FIGS. 1 and 3). The base unit 112 includes a container base 114, an opposing container top 116 (which defines the top of the storage container 100), and a pair of opposing container sidewalls 118 rising from the container base 114 to the container top 116. The container interior 104 is then situated between the container sidewalls 118, and between the container base 114 and the container top 116, and is bounded by these structures and by the container door 106.

Several features of the base unit 112 are beneficially adapted to enhance the use of the storage container 100 in a medical environment. First, the container base 114 is preferably sized with an area of less than approximately 2 square feet, and more specifically with a width of 12 inches or less between the sidewalls 118, and with a depth of 24 inches or less in the transverse direction. This ensures that the container base 114 is relatively compact and can relatively easily fit atop a portion of a medical service cart (e.g., a nurse's or anesthesiologist's cart) while leaving space atop the cart for medical files, medical instruments, or other matter. The somewhat elongated shape of the container base 114, as opposed to a square base or the like, makes more efficient use of cart space by allowing the storage container 100 to extend along the edge of a cart's platform without extending overmuch into the central area of the platform. (Medical personnel often find it convenient to leave a central area of the cart platform free to accommodate tools for addressing whatever tasks are at hand, or to accommodate an open file so that the central area of the platform effectively serves as a mobile desktop for writing purposes, etc.)

Second, at least a major portion of the container top 116 is sloped such that the container top 116 cannot stably support an object having a flat base atop the container top 116 (i.e., the container top 116 is sloped such that when the storage unit is placed on a medical cart, objects such as files, when placed atop the storage container 100, will slide off, particularly when the cart starts or stops motion). This serves to deter users from stacking files or other matter atop the storage container 100, which is preferably left as visible and as free from obstruction as possible so that medicines stored therein can better be readily accessed when needed.

The container door 106 is then preferably formed of a single piece of at least substantially transparent rigid material, or is otherwise windowed so that it is at least substantially transparent over at least a major portion of its area. The container door 106 has opposing upper and lower edges (the lower edge 120 being particularly visible in FIG. 2), and opposing arcuately curved side edges 122 which extend between the upper and lower edges, and which are slidably engaged within grooves 124 defined in the container sidewalls 118. The container door 106 may slide in the grooves 124 between an open position (as in FIG. 2), wherein an opening is defined between the container door 106 and the base unit 112 to allow access to the container interior 104, and a closed position (as in FIGS. 1 and 3), wherein the container door 106 and the base unit 112 enclose the container interior 104. As can be seen in the drawings, the container door 106 presents a curved surface to the user which will not support the placement of objects thereon, and which also provides both a frontal and a top view of the medicines stored within the container 100, which is useful if personnel need to make a rapid visual assessment of the medicines therein. In contrast, a container door having a corner defined therein will tend to introduce an obstacle or distortion into the user's view, even if such corner is formed of transparent material. Additionally, the curvature of the container door 106 is preferably slightly different from the curvature of the grooves 124, whereby some degree of friction exists between the container door 106 and the base unit 112 (particularly when formed of plastic) so that the container door 106 will generally remain in the position to which it is opened without falling shut, and at the same time it will easily open and close.

The container door 106 is preferably latchable and lockable in its closed position so that medicines may be secured against theft or loss. Most preferably, the storage unit includes a latch which is engageable between the container door 106 and the base unit 112, and wherein the latch has at least two separate modes of engagement and disengagement, such as by a key 108 insertable into one of the container door 106 and the base unit 112 for engaging and disengaging the latch, and also by a keyless entry means (e.g., a touchpad combination lock 126) for engaging and disengaging the latch without a key 108. This allows different modes of entry by different personnel, e.g., a pharmacist having a master key 108 may restock a group of storage containers, and the storage containers may then be distributed to nurses or other personnel, with each storage container 100 being openable by entering a combination (unique to the container 100 and to its user) on its keypad 126. The dual locking scheme is easily and inexpensively implemented in the manner best illustrated in FIG. 3, wherein a first latch 128—shown as a rotating bar actuated by the key 108 of FIG. 1, and which is spaced from the sidewall 118—rotates between a disengaged position (shown in phantom/dashed lines) spaced from the container base 114 and an engaged position closer to the container base 114. A second latch 130 extends from the keyless entry means (i.e., the keypad), and it may be situated in an engaged position wherein it extends closely adjacent to the sidewall 118, or in a disengaged position wherein it is withdrawn to a position closer to the keyless entry means. Thus, if the first (keyed) latch 128 is put in its engaged position with the container door 106 closed, and the second (keyless) latch 130 is then put in its engaged position, the second latch 130 interferes with the first latch 128 if one attempts to open the container door 106, and the container door 106 is effectively locked shut. At the same time, unlocking of the first latch 128 (i.e., using the key 108 to rotate it out of the path of the second latch 130), or unlocking the second latch 130 (i.e., actuating the keypad 126 to translate the second latch 130 so that it does not encounter the first latch 128 as the container door 106 is opened), will allow the container door 106 to be opened. In short, the first and second latches 128 and 130, when both in their engaged positions, engage the container door 106 to the base unit 112 when the container door 106 is in its closed position. On the other hand, when at least one of the first and second latches 128 and 130 is in its disengaged position, the container door 106 is slidable between its open and closed positions.

The storage container 100 is also preferably provided with a medication tray 102 (shown in FIGS. 1 and 2) which is insertable and removable within the container interior 104, and which is sized to fit on the container base 114 within the container interior 104 when the container door 106 is closed. Additionally, the medication tray 102 is preferably removably affixable to the container base 114 from within the container interior 104 (and not from the container exterior), as by providing one or more securement apertures 132 (see FIG. 3) within the container base 114 and then providing attachment means 134 (see FIG. 1) for extending into and engaging the securement apertures 132 within the container base 114. As illustrated by FIG. 1, this could be done by simply inserting a fastener 134 through the medication tray 102 and into a securement aperture 132 (visible only in FIG. 3) in the container base 114. The attachment means could alternatively take more complex forms such as a latch which pivots from the medication tray 102 into the securement aperture 132, a pin which engages the medication tray 102 to the container base 114 when inserted through the medication tray 102 and into the securement aperture 132 and then being rotated, or other forms as discussed elsewhere in this document. This feature allows personnel (e.g., pharmacy staff or medication control officers) to insert a stocked medication tray 102 into the container 100 and affix it therein in a manner whereby the medication tray 102 cannot be easily disengaged by one who only has access to the exterior of the storage container 100. More preferably, the attachment means extends through the medication tray 102, through any securement aperture(s) 132 in the container base 114, and then engages any service cart or other structure atop which the storage container 100 is situated. Thus, personnel may both secure the medication tray 102 within the storage container 100 and also secure the storage container 100 to a service cart or other structure at the same time, thereby better ensuring that both the medication tray 102 and the storage container 100 are not easily removed.

The storage container 100 also preferably includes a handle 136 on the container door 106 to ease opening and closing of the container door 106. It is useful to define a handle aperture 138 within the handle 136, and also provide a sealing aperture 140 in the base unit 112 closely adjacent the location at which the handle 136 rests when the container door 106 is in a closed position. This allows a security tag (e.g., a breakaway plastic seal, not shown) to extend through the handle aperture 138 and sealing aperture 140 when the container door 106 is closed, such that when the container door 106 is opened, the tag/seal will be broken to indicate that the interior of the container 100 has been accessed.

Further advantages, features, and objects of the invention will be apparent from the remainder of this document in conjunction with the associated drawings.

DETAILED DESCRIPTION OF PREFERRED VERSIONS OF THE INVENTION

Figure 1:
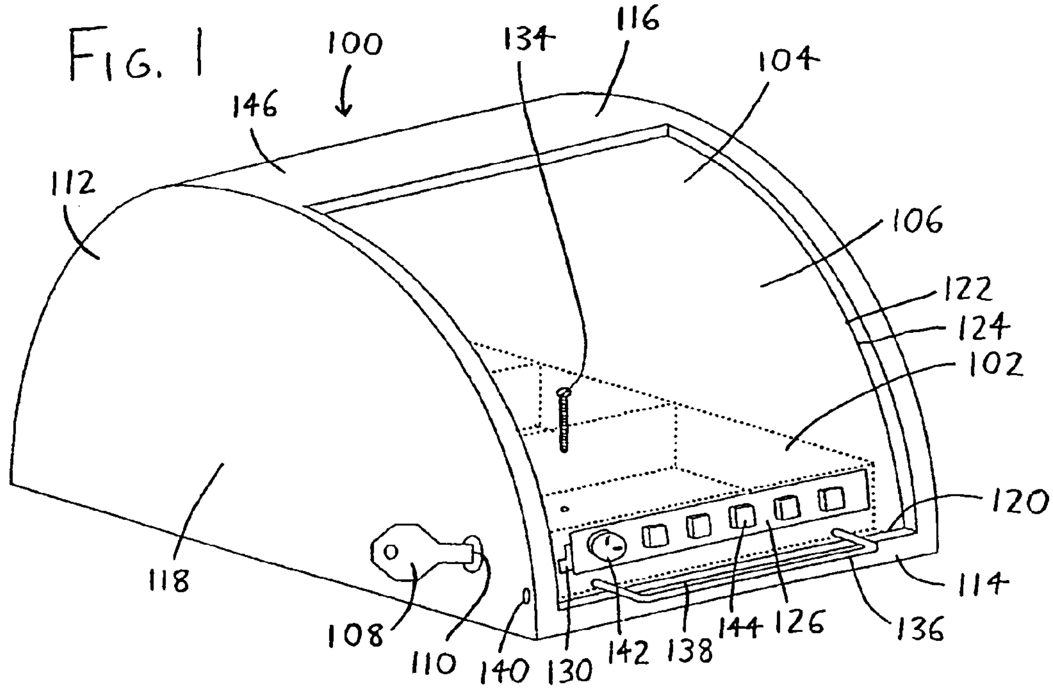
FIG. 1 is a perspective view of an exemplary preferred version of the invention, depicting a storage container 100 with a transparent container door 106 through which a medication tray 102 is visible, and showing a second latch 130 (which is actuated by the touchpad 126) in its disengaged position wherein it is spaced away from the adjacent sidewall 118 and from the first latch 128 shown in FIG. 3 (with the first latch 128 being actuated by the key 108), and thereby showing the container door 106 in a state wherein it is not latched to the base unit 112. Additionally, a fastener 134 used to secure the medication tray 102 to the base unit 102 (and also possibly to any service cart or other structure beneath the base unit 102) is shown exploded upwardly from the tray 102.
Figure 2:
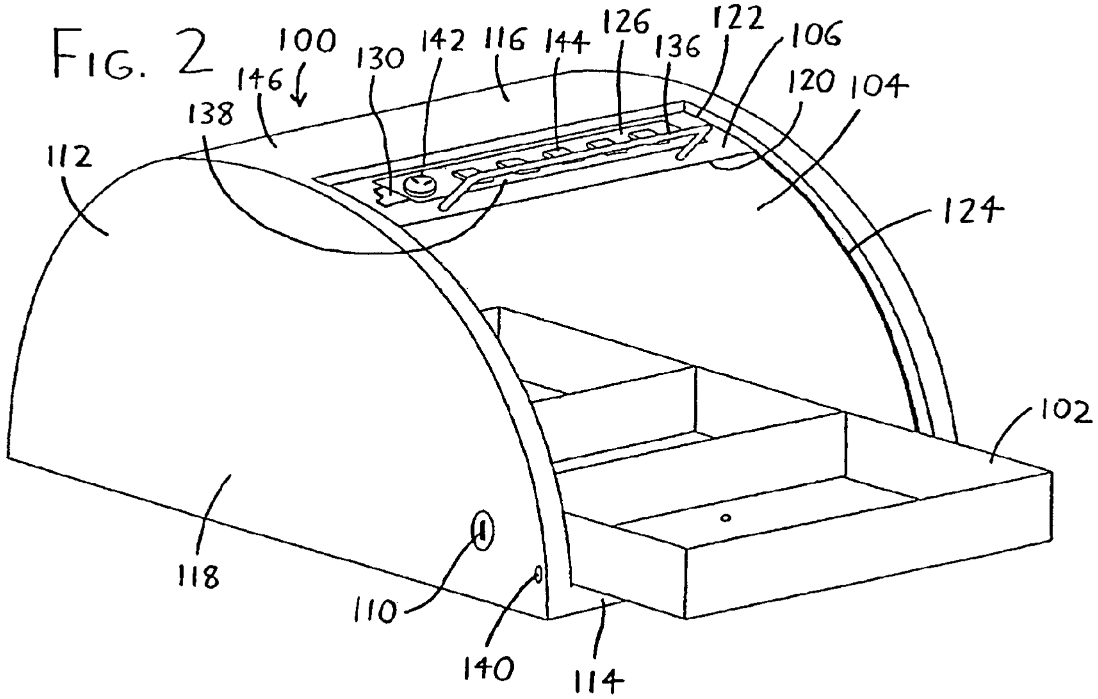
FIG. 2 is another perspective view of the storage container 100 of FIG. 1, wherein the container door 106 is open, and wherein the medication tray 102 is pulled outwardly from the container interior 104 (and the key 108 of FIG. 1 is removed).
Figure 3:
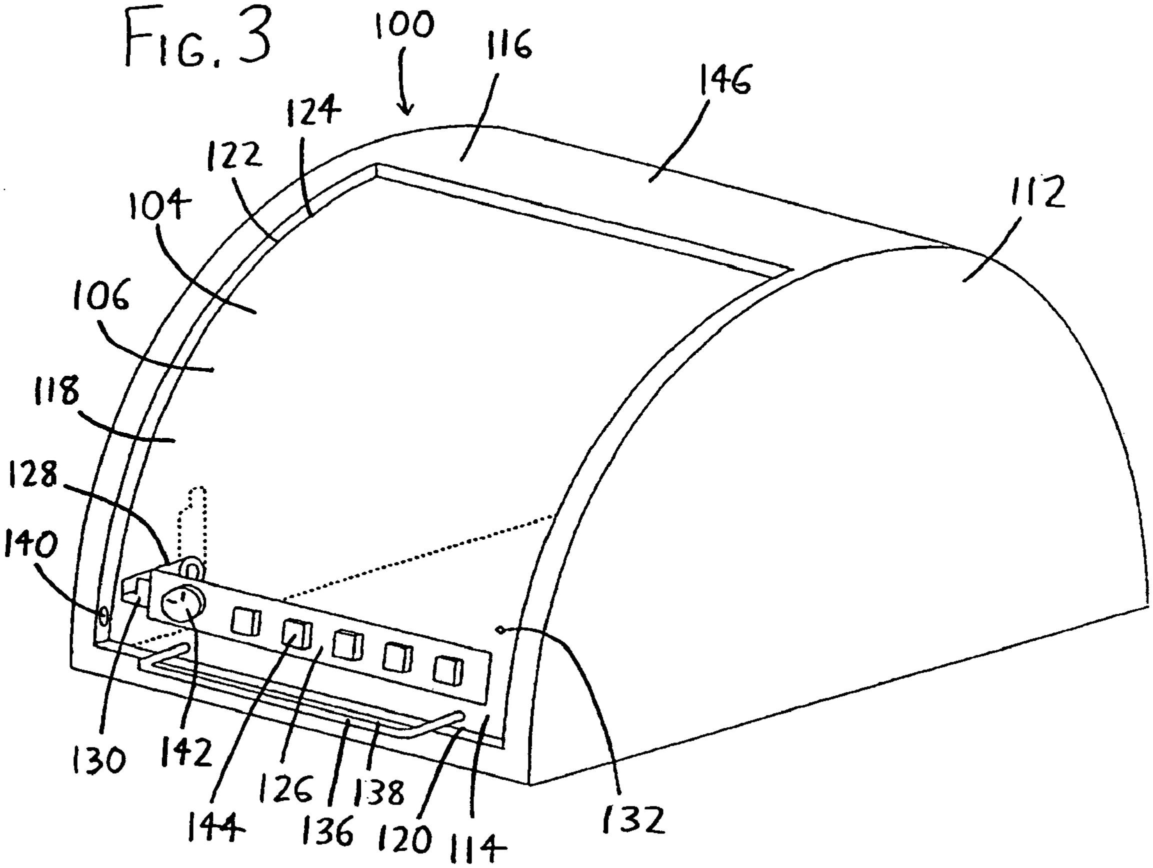
FIG. 3 is another perspective view of the storage container 100 of FIGS. 1 and 2 shown from its opposite side with the container door 106 closed (as in FIG. 1) and without the medication tray 102, and wherein both the first and second latches 128 and 130 are shown in their engaged positions (with the disengaged position of the first latch 128 being shown in phantom), whereby the container door 106 is effectively locked shut owing to interference between the first and second latches 128.

Regarding the version of the invention discussed above and shown in the drawings, the touchpad lock 126 operates as follows. The touchpad 126, which is merely a preferred version of a touchpad (with many variations being commercially available), includes a rotary knob 142 and a series of depressible buttons/keys 144. The keys 144 effectively serve to unlock the rotation of the knob 142 if the correct combination is entered on the touchpad 126, whereas rotation of the knob 142 moves the second latch 130 between its engaged and disengaged positions. Thus, if the second latch 130 is in its engaged position (extended adjacent the sidewall 118 below the first latch 128) and the user wishes to unlatch it, the user enters the correct combination on the touchpad 126, thereby unlocking the knob 142 and allowing it to be rotated to move the second latch 130 to its disengaged position. The container door 106 may then be opened. Rotating the knob 142 in the opposite direction moves the second latch 130 back into its engaged position, after which point the correct combination must again be entered on the touchpad keys 144 before the knob 142 can be rotated to move the second latch 130 back to its disengaged position.

The touchpad 126 for the second latch 130 is preferably solely mechanical (i.e., it needs no electrical power supply), with mechanical locks of this nature being available from a variety of combination lock manufacturers (and often being used on briefcases/luggage). A mechanical touchpad lock 126 is preferred because it is easily used by medication dispensing personnel without the need to locate keys and the like, and it is particularly easy to use after repeated use. Additionally, it may be easily reconfigured to provide a unique combination for the personnel using the container 100. However, other types of locks could be used instead, such as other types of mechanical combination locks (e.g., scroll-wheel combination locks, rotary dial combination locks, etc.), keyed locks (as with the first latch 128), etc. It is further not necessary that the lock for the second latch 130 be mechanical in nature, and electronic locks (such as touchpad locks similar to those found on door locks and safes) might be used instead. In this respect, to further restrict access to the container interior 104 solely to authorized personnel, the lock 126 could be a biometric one which reads characteristics such as fingerprints, retinal patterns, voice patterns, etc. Such a biometric lock could be provided in conjunction with an electronic memory for recording the identifying characteristics of the personnel opening (or attempting to open) the container 100, and/or wireless transmission of the identifying characteristics to some remote memory, so that the identities of users may be logged.

In similar respects, while a keyed first latch 128 is preferred because it allows a medication control officer, pharmacist, or other authorized party to bear a master key allowing entry to several containers 100 (a useful feature for personnel who need to stock several containers), the first latch 128 could instead be fixed in its engaged and disengaged states by other forms of locks. It is notable that keys need not take the form of conventional keys as depicted in the drawings, and alternative keys such as mechanical (e.g., punchcard-type) key cards or electronic (e.g., magnetic strip) key cards could be used instead.

Regarding the use of a seal/tag affixed between the handle aperture 138 and the sealing aperture 140 to indicate when the container drawer 106 has been opened (or that the container 100 has otherwise been tampered with), it is notable that such seals are readily available in the healthcare industry, with plastic breakaway seals being sold by suppliers such as Armstrong Medical Industries (Lincolnshire, Ill., USA). Such seals are beneficial because they allow a number of containers 100 to be stocked with medications for later use and then sealed, with the seal serving as an indication of whether or not the containers 100 have been tampered with. It should be understood that seams need not be affixed only between the handle aperture 138 and a sealing aperture 140 on the container sidewalls 118, and seals could be affixed between any region of the container door 106 and base unit 112. Containers can also be color-coded in accordance with facility standards, e.g., containers 100 can be color-coded to correspond to particular zones of a facility so that containers 100 which are taken outside of their authorized areas can be readily identified and relocated to their proper areas.

Other security features such as container tracking, as by radio frequency identification (RFID) tagging and/or barcode checkout, can also be added to containers 100. The containers 100 themselves may include RFID tags, barcodes, or other tracking means, or they may incorporate means for reading and/or logging trackable medications (e.g., medication bottles/containers bearing RFID tags and/or barcodes). Thus, if medication bottles/containers stored within the container 100 bear RFID tags, the container 100 might incorporate RFID readers which log the entry and exit of such bottles/containers. If the container 100 incorporates the aforementioned biometric lock, the container 100 might also log the identity of the person inserting or removing the tagged medication (and might provide an alarm or other signal if insertion or removal by unauthorized personnel occurs). If medication bottles/containers stored within the container 100 bear barcodes or similar machine-readable optical indicia, the container might also be provided with a scanner/reader for logging insertion and removal of the medication bottles/containers. Such a scanner/reader, if handheld, could also be used to read barcodes associated with the patient (e.g., on a patient's wristband or medical chart), and might provide an indication as to whether the proper medication is being delivered at the proper time. For example, if a caregiver accidentally removes the wrong medication from the container 100 and is about to administer it to a patient to whom the medication has not been prescribed, after scanning the medication and the patient information, the scanner might indicate the mismatch and provide a warning to the caregiver. A similar scheme could also be implemented with the aforementioned RFID tags.

As previously noted, it is useful to include some form of attachment means, such as the fastener 134 shown in FIG. 1, for attaching the medication tray 102 to the base unit 112 (and/or to attach the medication tray 102 and base unit 112 to a service cart, or to some other structure such as a patient's bedside table). While such attachment means is illustrated in the simple form of the fastener 134, it should be understood that the attachment means may take a wide variety of other forms instead of (or in addition to) fasteners. Attachment means which can be installed and removed from within the container interior 104 without the use of hand tools, but which are difficult to remove from the exterior of the container 100, are particularly preferred. As one example, a medication tray 102 might include a pivoting lever which, when actuated, extends through the securement aperture(s) 132 in the container base 114 to engage the service cart or other structure. As another example, pins or fasteners which have protrusions extending therefrom, and which can be inserted through the medication tray 102 and container base 114 into a service cart or other structure, can be rotated to engage to this structure and thereby affix the container 100 to the structure. Other forms of attachment means, such as pins or other extensions which bear retractable protrusions, or which are otherwise actuatable to expand and contract within securement apertures 132 and/or in apertures within service carts and other structures, could also or alternatively be used. Other types of attachment means requiring a greater amount of manipulation—for example, tie-down cords or buckled straps, resiliently flexible prongs/tabs which snap-lock into place, etc.—are also possible attachment means. The attachment means might also include some form of specialized bracket or other mounting structure which is affixed to carts, counters, or other structures whereupon containers are to be mounted, wherein the container 100 cooperates with such bracket or mounting structure to provide particularly rapid, easy, and/or tamper-free releasable attachment. Any or all of these attachment means could simply be used to affix the storage container 100 to the service cart or other structure, without also releasably attaching any medication tray 102 therein. It is emphasized that the ability to quickly attach and detach a container 100 to a cart, counter, or other structure is exceedingly useful, since it allows containers 100 to be readily stocked in a central location, distributed to locations of use and securely fixed down for use, and then readily be removed for cleaning and restocking when usage is completed. As an example, a hospital could review its surgery schedule for the day, stock an appropriate number of containers 100 for each procedure, and deliver each stocked container 100 to the place of its procedure. Once the procedures are complete, each container could be detached from its location and returned to the pharmacy (or other stocking site) for cleaning and restocking.

The container door 106 need not be transparent, and in fact it may beneficially be opaque where privacy regulations apply. One option is to include a pair of doors 106 which both slide in the grooves 124 immediately adjacent each other, with the outer door being translucent and the inner door being opaque, and perhaps with the inner opaque door being differently dimensioned so that it does not interfere with the action of the touchpad 126 and second latch 130. The inner opaque door could also be configured so that it could releasably attach to the outer transparent door (as by the use of snap-locking protrusions extending between the doors), or to the base unit 112 when in its fully opened position. Thus, the doors could act together as a unit to provide an effectively opaque door, or only the outer transparent door could be used (with the inner opaque door fixed in its fully opened position), so as to provide an effectively transparent door. Another option is to form an inwardly-extending lip on the interior surfaces of the container door 106 at its opposing edges 120, and then insert a sheet of resiliently flexible material—such as cardboard or thin semi-rigid plastic sheet—between the lips, with the sheet being bent to curve along the inner surface of the container door 106. If the rigidity of the curved sheet is sufficient, its inherent resilience will cause the sheet to engage the lips and bear against the inner surface of the container door 106 to remain thereon until removed. Alternatively, simpler measures can be taken to temporarily opaque the container door 106: some opaque covering material, such as an opaque reusable vinyl cling (or simply a taped piece of paper), could be affixed to the interior surface of the container door 106 to temporarily block visibility. It is also not necessary in all cases to opaque the door 106 to protect privacy. As an example, if the container door 106 is formed of some translucent filtering material (e.g., red translucent plastic), and if patient identifying information is printed on the medication bottles within the container 100 in the same color, the patient information will effectively be invisible when viewed through the container door 100, whereas other printing on the medication bottles (e.g., in black ink) will still be visible.

Since the version of the invention described above is merely a preferred one, it should be kept in mind that the container 100 can undergo a wide variety of changes in size and shape. As one example, the curved container top 116 was previously noted as being beneficial in that it serves as a deterrent to stacking objects atop the container 100, but this benefit could be achieved with other shapes as well, e.g., by having the container top 116 defined by the peak of triangular container sidewalls 118.

As another example of a configuration change, while the container 100 is shown with a fixed container ceiling 146 rising upwardly from the container base 114 opposite the container door 106, and extending between the container sidewalls 118, this container ceiling 146 (or a portion thereof) might be formed similarly to the container door 106, and may slide in grooves situated adjacent to the grooves 124 in which the container door 106 slides. This would effectively provide a container 100 with a pair of doors, either one allowing access to the container interior 104. In this case, it may be useful to lock the container 100 by latching the doors together, since doing so may effectively secure both doors in place at the same time.

As yet another example of a modification, the medication tray 102 need not be removable, and can simply be formed integrally with the container base 114. The base 114 and/or sidewalls 118 might include slots or other structures which releasably engage insertable dividers, such that a user may install dividers on the container base 114 to form a tray thereon which is reconfigurable as desired.

As a further example, the container door 106 could be hinged to the base unit 112 rather than sliding within the grooves 124, though the grooves 124 are useful to avoid or reduce crevices from which the container door 106 might be pried open.

The container 100 is preferably formed of durable materials which are sterilizable and which are resistant to corrosion from common antiseptic cleaning agents, with appropriate plastic, metal, and ceramic materials being preferred.

It should therefore understood that the invention is not intended to be limited to the preferred versions of the invention described above, but rather is intended to be limited only by the claims set out below. Thus, the invention encompasses all different versions that fall literally or equivalently within the scope of these claims.

What is claimed is:

1. A medication storage container comprising:

a. a base unit including:

(1) a container base, (2) an opposing container top defining the top of the container, (3) a pair of opposing container sidewalls rising from the container base to the container top, the container sidewalls having opposing grooves defined therein, wherein the container top is sloped downwardly from approximately the middle top portion of the container sidewalls to the container base to define a container back wall, wherein the container sidewalls, container back wall and container top define a substantially non-planar exterior top surface such that it cannot stably support an object having a flat base thereon; wherein a container interior is situated between the container sidewalls, the container back wall and between the container base and the container top;

b. a door formed of a single rigid piece, the door including:

(1) opposing upper and lower edges, and (2) opposing side edges each extending between the upper and lower edges, the side edges being slidably situated within the opposing grooves in the container sidewalls, whereby the door may slide in the grooves between (i) an open position wherein an opening is defined between the door and the base unit to allow access to the container interior, and (ii) a closed position wherein the door and the base unit enclose the container interior;

wherein the door is at least substantially transparent over at least a major portion of its area.

2. The medication storage unit of claim 1 wherein the container base is dimensioned:

a. with a width of no greater than 12 inches between the sidewalls, and b. with a depth of no greater than 24 inches transverse to the sidewalls.

3. The medication storage unit of claim 1 wherein the opposing side edges of the door are arcuately curved, whereby the door has a curved front surface extending between the side edges.

4. The medication storage unit of claim 1 further comprising a latch engageable between the door and the base unit, the latch being engageable and disengageable by:

a. a key insertable into one of the door and the base unit, and b. keyless entry means for engaging and disengaging the latch without a key.

5. The medication storage unit of claim 4 wherein the keyless entry means includes a touchpad.

6. The medication storage unit of claim 1 further comprising:

a. a first latch between the door and the base unit, the first latch being movable between engaged and disengaged positions by an insertable key; and b. a second latch between the door and the base unit, the second latch being movable between engaged and disengaged positions by a keyless entry means for engaging and disengaging the second latch without a key;

wherein:

(1) the first and second latches, when both in their engaged positions, engage the door to the base unit when the door is in its closed position, and (2) when at least one of the first and second latches is in its disengaged position, the door is slidable between its open and closed positions.

7. The medication storage unit of claim 1:

a. wherein one or more securement apertures are defined within the container base; and b. further comprising:

(1) a tray insertable and removable within the container interior, and (2) attachment means for engaging the tray within the container interior, the attachment means extending into the securement apertures within the container base.

8. The medication storage unit of claim 1:

a. further comprising a handle defined on the door, the handle having a handle sealing aperture therein; and b. a base sealing aperture defined in the base unit, the base sealing aperture being located closely adjacent the handle sealing aperture when the door is in its closed position.

9. A medication storage container comprising:

a. a base unit including:

(1) a container base having an area of less than 2 square feet, (2) an opposing container top defining the top of the container, (3) a pair of opposing container sidewalls rising from the container base to the container top, the container sidewalls having opposing grooves defined therein, wherein the container top is sloped downwardly from approximately the middle top portion of the container sidewalls to the container base to define a container back wall, wherein the container sidewalls, container back wall and container top define a substantially non-planar exterior top surface such that it cannot stably support an object having a flat base thereon; wherein a container interior is situated between the container sidewalls the container back wall and between the container base and the container top;

b. a door formed from a single rigid piece, the door being at least substantially transparent over at least a major portion of its area and including:

(1) opposing upper and lower edges, and (2) opposing side edges each extending between the upper and lower edges, the door being movably affixed to the base unit within the grooves to move between:

(i) an open position wherein an opening is defined between the door and the base unit to allow access to the container interior, and (ii) a closed position wherein the door and the base unit enclose the container interior.

10. The medication storage unit of claim 9 wherein the door has its side edges slidably engaged to the container sidewalls, whereby the door may slide along the sidewalls between its open and closed positions.

11. The medication storage unit of claim 9 further comprising a latch engageable between the door and the base unit, the latch being engageable and disengageable by:

a. a key insertable into one of the door and the base unit, and b. keyless entry means for engaging and disengaging the latch without a key.

12. The medication storage unit of claim 9 further comprising:

a. a first latch between the door and the base unit, the first latch being movable between engaged and disengaged positions by an insertable key; and b. a second latch between the door and the base unit, the second latch being movable between engaged and disengaged positions by a keyless entry means for engaging and disengaging the second latch without a key;

wherein:

(1) the first and second latches, when both in their engaged positions, engage the door to the base unit when the door is in its closed position, and (2) when at least one of the first and second latches is in its disengaged position, the door is slidable between its open and closed positions.

13. The medication storage unit of claim 12 wherein the keyless entry means includes a touchpad.

14. The medication storage unit of claim 9:

a. wherein one or more securement apertures are defined within the container base; and b. further comprising:

(1) a tray insertable and removable within the container interior, and (2) attachment means for engaging the tray within the container interior, the attachment means extending into the securement apertures within the container base.

15. The medication storage unit of claim 9:

a. further comprising a handle defined on the door, the handle having a handle sealing aperture therein; and b. a base sealing aperture defined in the base unit, the base sealing aperture being located closely adjacent the handle sealing aperture when the door is in its closed position.

16. A medication storage container comprising:

a. a base unit including:

(1) a container base, (2) an opposing container top defining the top of the container, (3) a pair of opposing container sidewalls rising from the container base to the container top, wherein the container top is sloped downwardly from approximately the middle top portion of the container sidewalls to the container base to define a container back wall, wherein the container sidewalls, container back wall and container top define a substantially non-planar exterior top surface such that it cannot stably support an object having a flat base thereon; wherein a container interior is situated between the container sidewalls the container back wall and between the container base and the container top;

b. a door including a single rigid piece of material having:

(1) opposing upper and lower edges, and (2) opposing arcuately curved side edges slidably engaged to the container sidewalls, whereby the door may slide along the sidewalls between:

(i) an open position wherein an opening is defined between the door and the base unit to allow access to the container interior, and (ii) a closed position wherein the door and the base unit enclose the container interior;

c. a first latch between the door and the base unit, the first latch being movable between engaged and disengaged positions by an insertable key; and d. a second latch between the door and the base unit, the second latch being movable between engaged and disengaged positions by a keyless entry means for engaging and disengaging the second latch without a key;

wherein:

(1) the first and second latches, when both in their engaged positions, engage the door to the base unit when the door is in its closed position, (2) when at least one of the first and second latches is in its disengaged position, the door is slidable between its open and closed positions.

17. The medication storage unit of claim 1 further comprising a tray insertable and removable within the container interior, the tray being removably affixable to the container base from within the container interior.

18. The medication storage container of claim 9 wherein the container base is dimensioned to have an area of no greater than 2 square feet.

19. A method for storing medication using the medication storage container of claim 1, including the steps of:

a. situating drugs within the container interior, and b. situating the door in the closed position with the drugs within the container interior.

* * * * *